US010052472B2

(12) United States Patent
Maurice

(10) Patent No.: US 10,052,472 B2
(45) Date of Patent: Aug. 21, 2018

(54) COUPLER FOR ENDOSCOPE FLUID SUPPLY

(71) Applicant: ERBE-USA, Inc., Marietta, GA (US)

(72) Inventor: Daniel G. Maurice, Monument Beach, MA (US)

(73) Assignee: ERBE-USA, Inc., Marietta, GA (US)

( * ) Notice: Subject to any disclaimer, the term of this patent is extended or adjusted under 35 U.S.C. 154(b) by 676 days.

(21) Appl. No.: 14/529,967

(22) Filed: Oct. 31, 2014

(65) Prior Publication Data

US 2016/0121095 A1 May 5, 2016

(51) Int. Cl.
A61M 39/26 (2006.01)
A61M 39/10 (2006.01)
A61B 1/00 (2006.01)
A61M 39/24 (2006.01)

(52) U.S. Cl.
CPC ......... A61M 39/10 (2013.01); A61B 1/00128 (2013.01); A61M 39/24 (2013.01); A61M 2039/1033 (2013.01); A61M 2039/1038 (2013.01)

(58) Field of Classification Search
CPC ............ A61M 39/10; A61M 2039/267; A61M 39/26; A61B 1/00128
USPC ........................................ 604/533, 535, 537
See application file for complete search history.

(56) References Cited

U.S. PATENT DOCUMENTS

| D239,025 S | 3/1976 | D'Alo |
| D245,921 S | 9/1977 | Beran |
| D266,790 S | 11/1982 | McCord |
| D271,618 S | 11/1983 | Nishigaki |
| D300,361 S | 3/1989 | Tokarz |
| 4,828,295 A * | 5/1989 | Plaquin ................. E21B 17/042 264/162 |
| D302,729 S | 8/1989 | Stephens et al. |
| 5,151,101 A | 9/1992 | Grossi et al. |
| D340,316 S | 10/1993 | Zdrok |
| D472,630 S | 4/2003 | Douglas et al. |
| D496,998 S | 10/2004 | Pajunk et al. |
| D612,496 S | 3/2010 | Bennison |
| D613,403 S | 4/2010 | Poll et al. |
| D624,181 S | 9/2010 | Harata et al. |
| D636,079 S | 4/2011 | Leypold et al. |
| D652,923 S | 1/2012 | Kennedy et al. |
| D657,870 S | 4/2012 | Becker |
| 8,152,790 B2 | 4/2012 | Lopez et al. |
| 8,206,375 B2 | 6/2012 | Snow |

(Continued)

Primary Examiner — Deanna K Hall
(74) Attorney, Agent, or Firm — Cooley LLP

(57) ABSTRACT

In some embodiments, a device for coupling a fluid source to a medical device includes a housing. The housing includes a proximal portion and a distal portion and defines a passageway therebetween. The proximal portion is configured to be coupled to the fluid source and the distal portion is configured to be coupled to the medical device such that the medical device is in fluidic communication with the fluid source via the passageway. A deformable member is disposed on the distal portion and is configured to deform to removably couple the housing to the medical device. In some embodiments, the deformable member is configured to form a substantially fluid-tight seal with the medical device. In some embodiments, the distal portion includes a sealing member configured to form a substantially fluid-tight seal with the medical device.

18 Claims, 13 Drawing Sheets

(56) References Cited

U.S. PATENT DOCUMENTS

| | | |
|---|---|---|
| D676,544 S | 2/2013 | Blocher |
| D678,521 S | 3/2013 | Mort et al. |
| D693,465 S | 11/2013 | Koehler et al. |
| D712,014 S | 8/2014 | Guest |
| D717,432 S | 11/2014 | Leroy et al. |
| D719,650 S | 12/2014 | Arinobe et al. |
| D732,664 S | 6/2015 | Vvoehr et al. |
| D739,527 S | 9/2015 | Chauvette |
| 2007/0161970 A1* | 7/2007 | Spohn .................. A61M 5/007 604/533 |
| 2010/0125164 A1 | 5/2010 | LaBombard |
| 2012/0088974 A1 | 4/2012 | Maurice |

* cited by examiner

COUPLER FOR ENDOSCOPE FLUID SUPPLY

BACKGROUND

Embodiments described herein relate generally to devices for coupling a fluid source to a medical device, and in particular to couplers that include at least a portion which deforms to enable coupling with the medical device.

Many medical devices such as, for example, endoscopes, catheters, ultrasonic probes, etc. define a fluidic channel to communicate a fluid from a proximal end to a distal end of the medical device. For example, some endoscopes define a fluidic channel for carrying a fluid, for example, water, physiological saline, or any other solution from a proximal end of the endoscope such as, for example, a control handle or light guide connector, through an insertion tube, and out of a distal tip of the endoscope. The fluid can be used for washing a lens of the endoscope, clearing obstructions, irrigating a target tissue, or providing lubrication for *facile* movement of the endoscope within a bodily lumen.

Conventional endoscopes generally include a coupling member or otherwise coupling portion which is coupled to a fluid source using a coupler, for example, a male coupler or a female coupler. Conventional couplers generally include threads configured to mate with corresponding threads defined by the coupling portion of the medical device and form a substantially fluid-tight seal when the coupler is coupled to the medical device. Conventional couplers are generally rigid members formed from rigid materials, for example, threaded rigid plastic or metals (e.g., stainless steel, aluminum, copper, etc.), TEFLON® or other suitable materials. Such conventional couplers (non-metalic), however, are commonly cross-threaded which can lead to wear and tear of threads. Furthermore, repeated use also contributes to the wear and tear of the threads. Because of this, conventional couplers are prone to leaking and can even be loosened during a medical procedure due to manipulations of the endoscope. A coupler that is loosened, cross-threaded or leaks may need to be replaced during the medical procedure. Such interruptions can distract the medical professional performing the medical procedure causing errors and prolonging the medical procedure.

Thus, there is a need for new couplers which are reliable, suffer from limited or negligible wear and tear, and have a long life.

SUMMARY

Embodiments described herein relate generally to devices for coupling a fluid source to a medical device, and in particular to couplers that include at least a portion which deforms to enable coupling with the medical device. In some embodiments, a device for fluidically coupling a fluid source to a medical device includes a housing. The housing includes a proximal portion and a distal portion and defines a passageway therebetween. The proximal portion is configured to be coupled to the fluid source and the distal portion is configured to be coupled to the medical device such that the medical device is in fluidic communication with the fluid source via the passageway. A deformable member is disposed on the distal portion and is configured to deform and removably couple the housing to the medical device. In some embodiments, the deformable member is configured to form a substantially fluid-tight seal with the medical device. In some embodiments, the distal portion includes a sealing member configured to form a substantially fluid-tight seal with the medical device.

DETAILED DESCRIPTION

Figure 1:
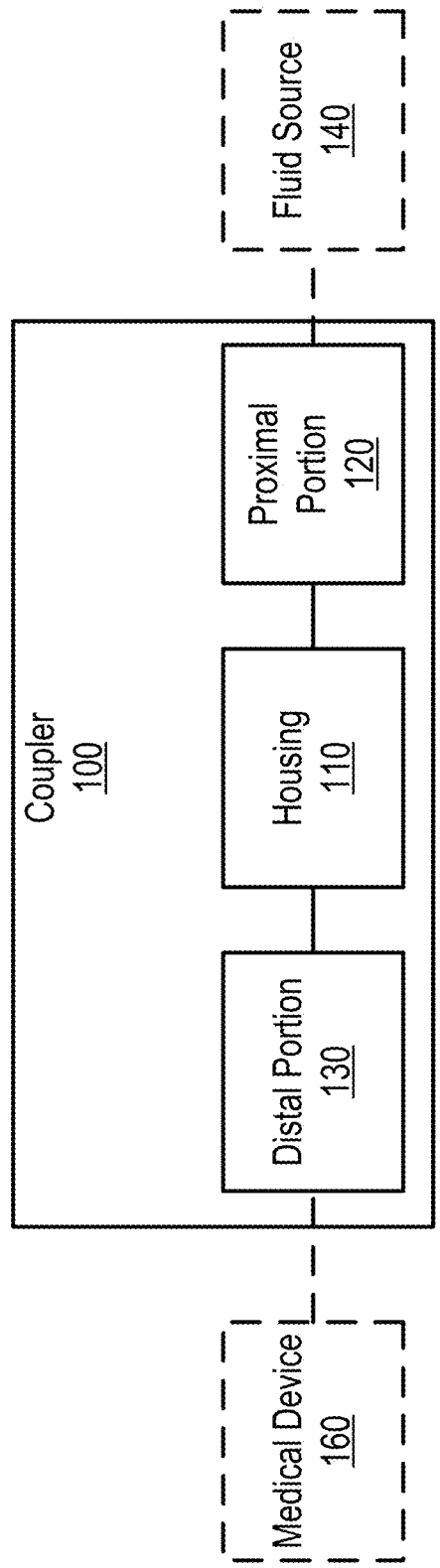
FIG. 1 is a schematic illustration of a coupler, according to an embodiment.

Embodiments described herein relate generally to devices for coupling a fluid source to a medical device, and in particular to couplers that include at least a portion which deforms to enable coupling with a medical device. Conventional medical devices such as, for example, endoscopes generally include a coupling member or otherwise coupling portion which is coupled to a fluid source using a coupler, for example, a male coupler or a female coupler. Conventional couplers generally include threads configured to mate with corresponding threads defined by the coupling portion of the medical device and form a substantially fluid-tight seal with the coupling portion. Conventional couplers are generally rigid members formed from rigid materials, for example, threaded rigid plastic or metals (e.g., stainless steel, aluminum, copper, etc.), TEFLON® or other suitable materials. Such conventional couplers, however, are commonly cross-threaded which can lead to wear and tear of threads. Furthermore, repeated use also contributes to the wear and tear of the threads. Because of this, conventional couplers are prone to leaking and can even be loosened during a medical procedure due to manipulations of the endoscope. A coupler that is loosened, cross-threaded or leaks may need to be replaced during the medical procedure. Such interruptions can distract the medical professional performing the procedure which can lead to errors and also prolong the procedure.

Embodiments of the couplers described herein include at least a portion which deforms when the coupler is coupled to the medical device (e.g., an endoscope). Such couplers do not include threads but instead, include a deformable portion or member which deforms, for example, to conform to a threaded portion of the medical device. Embodiments of the couplers described herein provide several advantages over conventional couplers including, for example: (1) coupling to a medical device without requiring threads which minimizes or eliminates wear and tear of the coupler; (2) maintaining fluidic sealing between the coupler and the medical device even after repeated use; (3) providing longer life in comparison with conventional couplers; (4) deforming for coupling to the medical device thereby, allowing the coupler to be coupled to medical devices that include coupling members or otherwise coupling portions of various shapes and sizes; (5) providing male and female deformable couplers such that the coupler can be coupled to any medical device that includes either a male or a female coupling member or otherwise coupling portion; and (6) allowing simple press-fit coupling of the coupler with the medical device, thereby enabling the coupling to be performed in a facile and rapid fashion.

In some embodiments, a device for fluidically coupling a fluid source to a medical device includes a housing. The housing includes a proximal portion and a distal portion which define a passageway therebetween. The proximal portion is configured to be coupled to a fluid source and the distal portion is configured to be coupled to a medical device such that the medical device is in fluidic communication with the fluid source via the passageway. The housing also includes a deformable member disposed on the distal portion. The deformable portion is configured to deform and removably couple the housing to the medical device. In some embodiments, the deformable member is configured to form a substantially fluid-tight seal with the medical device. In some embodiments, the distal portion includes a sealing member configured to form a substantially fluid-tight seal with the medical device.

In some embodiments, a device for fluidically coupling a fluid source to a medical device includes a housing. The housing includes a proximal portion and a distal portion which define a passageway therebetween. The proximal portion is configured to be coupled to the fluid source. The distal portion includes a protrusion configured to be coupled to the medical device such that the medical device is in fluidic communication with the fluid source via the passageway. A deformable member is disposed on the protrusion and configured to deform to removably couple the housing to the medical device. In some embodiments, the medical device includes a coupling portion having a plurality of female threads such that the deformable member is configured to deform and mate with at least a portion of the plurality of female threads to removably couple the housing to the medical device. In some embodiments, the deformable member is configured to form a substantially fluid-tight seal with the medical device. In some embodiment, a sealing member is also disposed on the protrusion distally from the deformable member and configured to form a substantially fluid-tight seal with the medical device.

In some embodiments, a device for fluidically coupling a fluid source to a medical device includes a housing. The housing includes a proximal portion and a distal portion which define a passageway therebetween. The proximal portion is configured to be coupled to the fluid source and the distal portion is configured to be coupled to the medical device such that the fluid source and the medical device are in fluid communication via the passageway. The distal portion defines a recess configured to receive at least a portion of the medical device when the distal portion is coupled to the medical device. A deformable member is disposed in the recess and configured to deform to couple the housing to the medical device. In some embodiments, the deformable member is configured to exert a force on a portion of the medical device disposed in the recess to prevent the medical device from uncoupling from the housing. In some embodiments, the deformable member is configured to form a substantially fluid tight seal with the medical device. In some embodiments, a sealing portion is also disposed in the recess and configured to substantially deform to form a substantially fluid-tight seal between the housing and the medical device.

As used in this specification, the terms "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device.

As used herein, the term "deforms", "substantially deforms" or "deformable" relates to the capacity of an object to deflect, bend, compress, or otherwise change shape in response to an applied force. For example, when a "rigid" or substantially incompressible object is impinged on a substantially deformable object or article, the substantially deformable object or article can deflect, bend, compress, or otherwise change shape, for example, to conform to a surface of the rigid object. Deformation or deformability is an extensive property of the object being described and thus, is dependent upon the materials from which the object is formed. For example, the deformability of an object can be increased or decreased by selectively including in the object, or forming the object from a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material which has a high hardness will not deform as much as a material having a low hardness in the presence of an equally applied force or otherwise stress. Thus, the deformability of the object can be increased by introducing into the object and/or constructing the object of a material having a relatively low hardness and high modulus of elasticity. In discussing the hardness and the subsequent effect on the deformability of an object, the Shore durometer scale is generally used. There are several scales for durometers with two commonly used in describing plastics, polymers, elastomers, and/or rubbers, namely, type A and type D, where type A is generally used for softer materials and type D is generally used for harder materials. The Shore durometer of a material is denoted by a number between 0 and 100, with higher numbers indicating a harder material, followed by the type of scale. For instance, a first material can be measured as having a Shore durometer of 40 Shore A and a second material can be measured as having a Shore durometer of 60 Shore D. Therefore, according to the Shore durometer scale, the second material is harder and thus, less deformable than the first material.

As used herein, the term "fluid-tight" is understood to encompass a seal that is liquid-impervious. The term "substantially" when used in connection with "fluid-tight," and/or "liquid-impervious" is intended to convey that, while total fluid imperviousness is desirable, some minimal leakage due to manufacturing tolerances, or other practical considerations (such as, for example, the pressure applied to the seal and/or within the fluid), can occur even in a "substantially fluid-tight" seal.

FIG. 1 shows a schematic illustration of a coupler 100, according to an embodiment. The coupler 100 includes a housing 110. The housing 110 includes a proximal portion 120 and a distal portion 130 and defines a passageway (not shown) therebetween. The proximal portion 120 is configured to be coupled to a fluid source 140, and the distal portion 130 is configured to be coupled to a medical device 160 such that the medical device 160 and the fluid source 140 can be in fluidic communication via the passageway.

The housing 110 or at least a portion of the housing 110 (e.g., a deformable member included in the distal portion 130, as described herein) can be formed from a deformable material such as, for example, an elastomer, polyurethane, silicone, rubber, urethane (e.g., QFLEX-ARP-90A-00-009 urethane) any other deformable material or combination thereof. In some embodiments, the hardness of the material or materials used alone or in combination thereof to form the housing 110 can be can be at least about 40 A, at least about 50 A, at least about 60 A, at least about 70 A, at least about 80 A, or at least about 90 A, inclusive of all ranges and values therebetween. In some embodiments, the hardness of the material used to form the housing 110 can be at least about 90 A. The housing 110 can have any shape or size. For example, in some embodiments, the housing 110 can be substantially cylindrical and define a circular, square, elliptical, oval, or otherwise polygonal cross section. Furthermore, an outer surface of the housing 110 can be tapered or contoured, for example, taper outwards from the distal portion 130 to the proximal portion 120. For example, the proximal portion 120 of the housing 110 can be wider, have a larger diameter, or have a larger cross-section than the distal portion 130 of the housing 110 such that the outer surface of the housing 110 tapers outwards from the distal portion 130 to the proximal portion 120. In some embodiments, a plurality of detents or otherwise depressions can be defined on an outer surface of the housing 110. The detents or otherwise depressions can serve as grips to facilitate coupling of the housing 110 the medical device 160 and/or the fluid source 140. The passageway can be defined through the housing 110, for example, from the proximal portion 120 to the distal portion 130 to allow the fluid to be communicated from the fluid source 140 to the medical device 160 via the housing 110. In some embodiments, the passageway can also be configured to receive at least a portion of a fluidic connector, as described herein.

The proximal portion 120 is configured to be coupled to the fluid source 140. For example, a proximal end of the passageway disposed within the proximal portion 120 can be configured to receive a distal end portion of a fluidic connector (not shown). The fluidic connector can include a Luer-lock connector, a threaded connector, a snap fit connector, a friction fit connector, or any other suitable connector configured to be coupled to the fluid source 140. The distal end portion of the fluidic connector can, for example, include a nozzle or a protrusion which can be disposed in the proximal end of the passageway. The distal end portion of the fluidic connector can define a lumen configured to establish fluidic communication between the fluid source 140 and the medical device 160 via the passageway. In some embodiments, the fluidic connector can be removably coupled to the proximal portion 120. For example, the proximal portion 120 can include a snap-fit mechanism, a friction-fit mechanism, threads, or a deformable portion, configured to couple the distal end portion of the fluidic connector to the proximal portion 120. In some embodiments, the fluidic connector can be fixedly coupled to the proximal portion 120. For example, the distal end portion of the fluidic connector can be fixedly coupled to the proximal end of the passageway using an adhesive, welding, heat sealing, fusion bonding, solvent welding, or monolithically formed with the housing 110. In some embodiments, a valve can be disposed in the passageway and configured to prevent any backflow of fluid from the medical device 160 to the fluid source 140. For example, a valve, for example, a check-valve, a ball-check valve, a diaphragm valve, a butterfly valve, a septum valve or any other valve can be disposed in the fluidic connector. The valve can, for example, be configured to allow fluid flow in only one direction, for example, from the fluid source 140 to the medical device 160, thereby preventing any back flow of fluid from the medical device 160 to the fluid source 140.

The distal portion 130 is configured to be coupled to the medical device 160. A deformable member 136 is disposed on the distal portion 130 and configured to deform and removably couple the housing 110 to the medical device 160. For example, the deformable member 136 can be formed from a substantially deformable material such as, for example, an elastomer, polyurethane, silicone, rubber, urethane (e.g., QFLEX-ARP-90A-00-009 urethane) any other deformable material or combination thereof. In some embodiments, the hardness of the material used to form the deformable member 136 can be less than about 50 A, less than about 60 A, less than about 70 A, less than about 80 A, or less than about 90 A, inclusive of all ranges (40 A to 90 A) and values therebetween. In some embodiments, the deformable member 136 can be configured to form a substantially fluid-tight seal with the medical device 160. In some embodiments, a sealing member (not shown) can also be disposed on the distal portion 130 of the housing 110 and configured to form a substantially fluid-tight seal with the medical device 160. Said another way, the deformable member 136 and the sealing member can collectively be configured to provide a double seal, thus forming a substantially fluid-tight seal between the housing 110 and the medical device 160. In some embodiments, the medical device 160 can include a coupling portion or otherwise coupling member having a plurality of male threads. In such embodiments, the deformable member 136 can be configured to deform and mate with at least a portion of the plurality of male threads to couple the housing 110 to the medical device 160. Similarly, in some embodiments, the medical device 160 can include a coupling portion or otherwise coupling member having a plurality of female threads. In such embodiments, the deformable member 136 can be configured to deform and mate with at least a portion of the plurality of female threads to couple the housing 110 to the medical device 160. In some embodiments, the housing 110 can be coupled to the medical device 160 without having to rotate the housing 110 and/or the medical device 160, for example, via press fitting the housing 110 into the medical device 160 or vice versa. In some embodiments, the housing 110 can be rotated relative to the threads without loosening and/or compromising the fluid-tight seal.

In some embodiments, the coupler 100 can be a male coupler which can be configured to be coupled to a female coupling member or otherwise female coupling portion of the medical device 160. In such embodiments, the distal portion 130 can include a protrusion configured to be coupled to the medical device 160. The passageway can also be defined through the protrusion such that the medical device 160 is in fluidic communication with the fluid source 140 via the passageway. The protrusion can extend away from the distal portion 130 and sized and shaped to be inserted into a lumen of a female coupling member of the medical device 160. In such embodiments, the deformable member 136 can be disposed on the protrusion and configured to deform to couple the housing 110 to the medical device. The deformable member 136 can, for example, include a ridge or a wall disposed about the cross-section of the protrusion and configured to deform when the protrusion is inserted (e.g., press fitted) into the lumen of the female coupling member. For example, the deformable member 136 can deform when the protrusion is inserted into the lumen defined by the female coupling member and conform to an inner surface of the lumen. The deformation can, for example, create a high friction interface with the inner surface of the lumen, which can removably couple the housing 110 to the medical device 160. In some embodiments, the protrusion can be tapered distally relative to the distal portion, for example, define a taper angle of about 1 degrees, 2 degrees, 3 degrees, 4 degrees, 5 degrees, or any other suitable taper angle. In this manner, when the protrusion is inserted or pressed into the lumen of the female coupling member, the deformation of the deformable member 136 and/or an elastic force exerted by the deformable member 136 against the lumen or an inlet of the lumen of the female coupling member can increase. In some embodiments, a plurality of deformable members 136 can be disposed on the protrusion. For example, a plurality of deformable members 136 can be disposed along the length of the protrusion space apart by a predetermined distance. Each of the plurality of deformable members 136 can be configured to deform when the protrusion is inserted into the lumen of the female coupling member and couple the housing 110 to the female coupling member and, thereby the medical device 160. Moreover, the plurality of deformable members 136 can enable formation of a substantially fluid-tight seal between the housing 110 and the medical device 160. In some embodiments, the medical device 160 can include a female coupling member (or otherwise a coupling portion) having a plurality of female threads such that the deformable member 136 is configured to deform and mate with at least a portion of the plurality of female threads to couple the housing 110 to the medical device 160. In some embodiments, the deformable member 136 can also form a substantially fluid-tight seal with the medical device 160, for example, the plurality of female threads of the coupling member. For example, the protrusion can be inserted into the lumen of the female coupling member with a suitable insertion force, for example, an insertion force of about 5 lbs., 6 lbs., 7 lbs., 8 lbs., 9 lbs., 10 lbs., or any other suitable force such that the deformable member 136 can form a substantially fluid-tight seal against the plurality of female threads of the female coupling member. Similarly stated, in some embodiments, the housing 110 can be coupled to the medical device 160 using manual force without using tools, such that the manual force is sufficient to urge the deformable member 136 to form a fluid tight seal with the lumen of the female coupling member. In some embodiments, the housing 110 does not have to be rotated to insert the protrusion into the lumen of the female coupling member and to urge the deformable member 136 to deform and removably couple the housing 110 to the medical device 160 via the female coupling member. For example, the protrusion can be press-fitted into the lumen defined by the female coupling member. In some embodiments, a sealing member can also be disposed on the protrusion distal from the deformable member 136. In some embodiments, the sealing member can include a circular rib resembling an O-ring and formed monolithically with the protrusion. In some embodiments, the sealing member can include an O-ring disposed in a circumferential groove defined on the protrusion. The sealing member can be configured to form a substantially fluid-tight seal with the medical device 160, for example, the lumen of the female coupling member of the medical device 160. For example, the sealing member can be disposed distally relative to the plurality of female threads defined by the lumen of the female coupling member and configured to form a substantially fluid-tight seal with the lumen of the female coupling member. In some embodiments, the sealing member can be substantially rigid such that it does not deform when disposed within the lumen of the female coupling member. In some embodiments, the sealing member can be formed from a substantially deformable material, for example, from the same material used to form the deformable member 136.

In some embodiments, the coupler 100 can be a female coupler which can be configured to be coupled to a male coupling member or otherwise male coupling portion of the medical device 160. In such embodiments, the distal portion 130 can define a recess configured to receive at least a portion of the medical device 160, for example, a proximal end portion of a male coupling member included in the medical device 160 when the housing 110 is coupled to the medical device 160. In some embodiments, the recess can have an inner diameter, width or otherwise cross-section which can be substantially smaller than an outer diameter, width or otherwise cross-section of the portion of the medical device 160 disposed in the recess, for example, the proximal end portion of the male coupling member. In such embodiments, the distal portion 130 can be configured to deform to removably couple the housing 110 to the medical device 160. In some embodiments, the portion of the medical device 160 disposed in the recess, for example, the proximal end portion of the male coupling member included in the medical device 160 can include a plurality of male threads. In such embodiments, an inner surface of the recess can be configured to deform to mate with the plurality of male threads and removably coupling the housing 110 to the medical device 160.

The deformable member 136 can be disposed in the recess and configured to deform to couple the housing 110 to the medical device 160. In some embodiments, the deformable member 136 can include a substantially planar member which can resemble a flap. The deformable member 136 can be disposed at an entrance of the recess and position orthogonal to the recess. The deformable member 136 can be configured to deform, for example, bend, when a portion of the medical device 160, for example, the proximal end portion of the male coupling member is inserted (e.g., press fitted) into the recess defined by the distal portion 130. In some embodiments, the deformable member 136 can be configured to exert a force on a portion of the medical device 160, for example, the proximal end portion of the male coupling member, to prevent the medical device 160 from uncoupling from the housing 110. In some embodiments the deformable member 136 can form a substantially fluid-tight seal with the medical device 160, for example, the proximal end portion the male coupling member of the medical device 160. In some embodiments, the deformable member 136 can be configured to exert a force, for example, a force of about 3 lbs., 4 lbs., 5 lbs., 6 lbs., 7 lbs., 8 lbs., 9 lbs., or 10 lbs., inclusive of all ranges therebetween on the medical device 160, for example, the portion of the medical device 160 disposed in the recess (e.g., the proximal end portion of the coupling member) to prevent the medical device 160 from uncoupling from the housing 110. For example, the deformable member 136 can return to its undeformed position once the proximal end portion of the male coupling member is disposed in the recess. The deformable member 136 can then apply a force on the proximal end portion of the male coupling member preventing uncoupling, for example, inadvertent or accidental coupling of the male coupling member from the housing 110 until a substantial force above a predetermined threshold is applied on the male coupling member or otherwise the medical device 160. In some embodiments, the force can be sufficiently high to overcome fluidic backpressure experienced by the housing 110, and/or the male coupling member. The force can however, be low enough such that manual force can be used to uncouple or couple the housing 110 to the medical device 160 (i.e., coupling the housing to the male coupling member of the medical device 160). In some embodiments, the deformable member can define a plurality of slots configured to allow deformation (e.g., increase or otherwise enhance the deformation) of the deformable member.

In some embodiments, a sealing portion can be disposed in the recess and configured to deform and form a substantially fluid-tight seal with the medical device (e.g., a portion of the proximal end portion of the male coupling member disposed in the recess). For example, at least a portion of an inner surface of the recess (e.g., proximate to the passageway) can be substantially deformable, for example, formed from a substantially deformable material such as urethane, and thus form the sealing portion. The sealing portion can deform and thereby, conform to an outer surface of a portion of the proximal end portion of the male coupling member in contact with the sealing portion. In this manner, the sealing portion can form a substantially fluid-tight seal between the housing 110 and the medical device 160.

The fluid source 140 can include any fluid source configured to deliver a fluid, for example, water, saline, dyes, etc. to the medical device 160. Suitable fluid sources can include a syringe, a syringe pump, a peristaltic pump, a rotary pump, a positive displacement pump, any other suitable pump or combination thereof.

The medical device 160 can be any suitable medical device configured to perform a medical procedure and/or deliver a fluid to a target tissue. For example, in some embodiments, the medical device 160 can include an endoscope. In some embodiments, the medical device 160 can include a catheter, an ultrasonic probe, a laparoscopic surgery tool, or any other medical device.

Having described above various general principles, several exemplary embodiments of these concepts are now described. These embodiments are only examples, and many other configurations of deformable couplers are contemplated.

Figure 2:
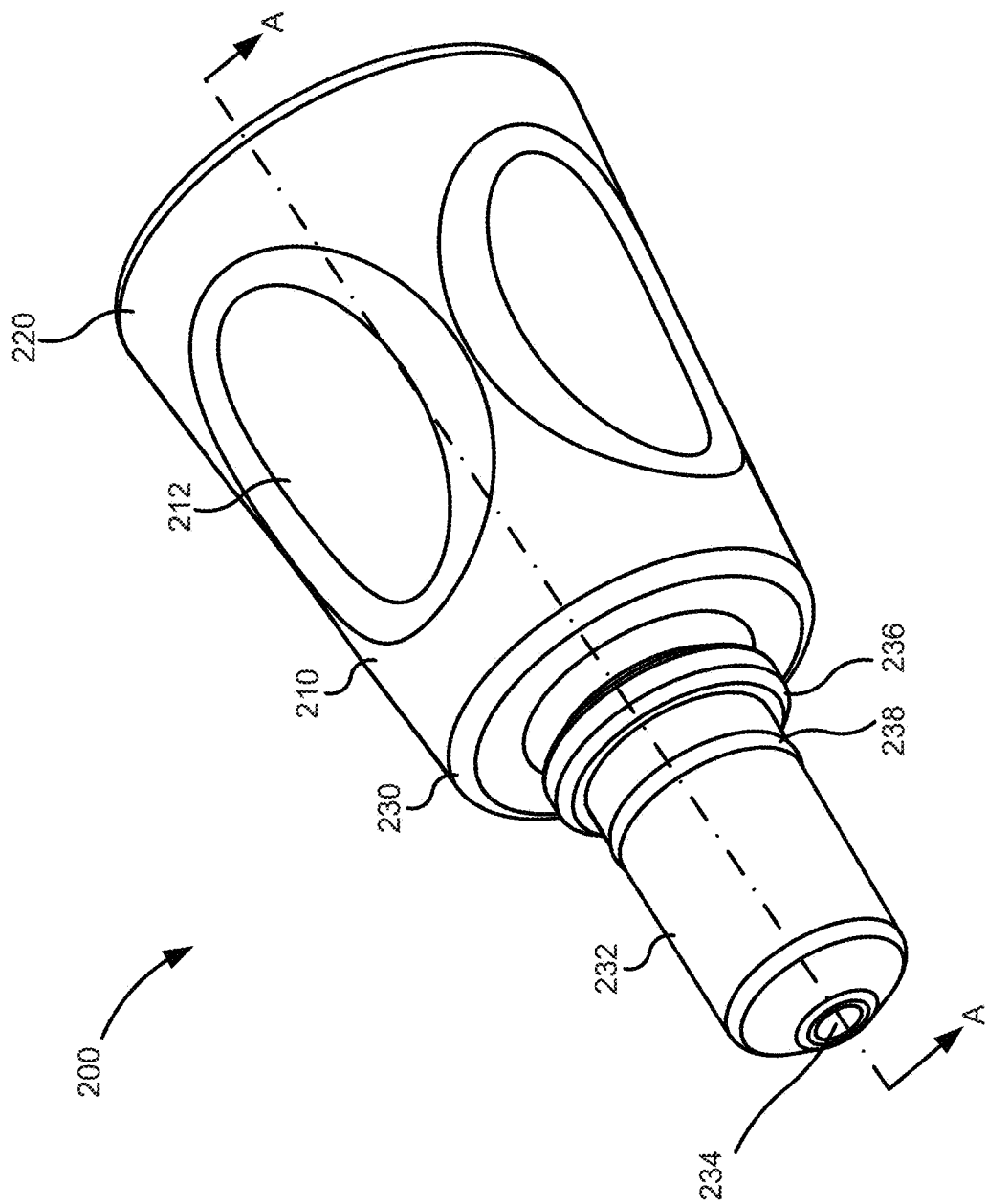
FIG. 2 is a front perspective view of a coupler, according to an embodiment.
Figure 3:
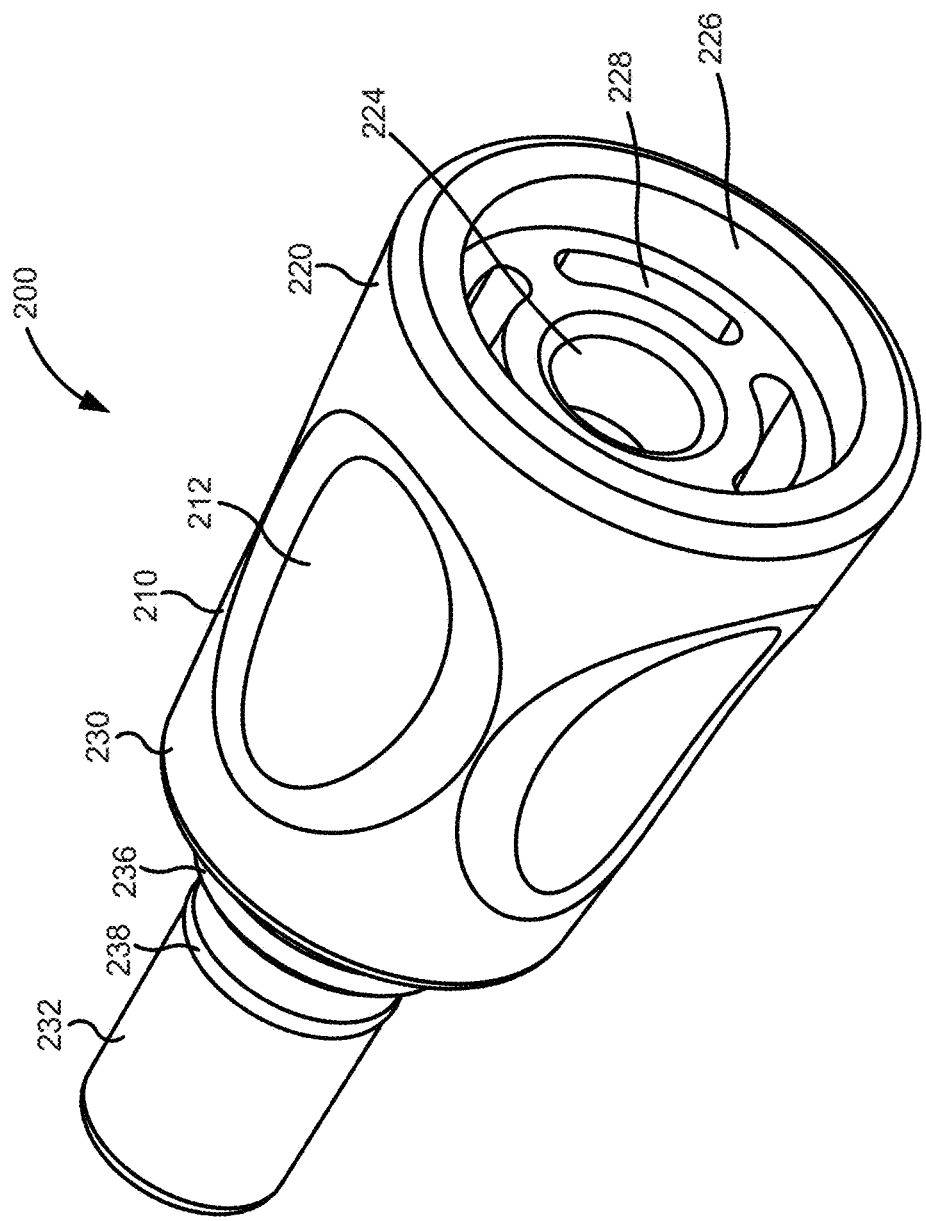
FIG. 3 is a back perspective view of the coupler of FIG. 2.
Figure 4:
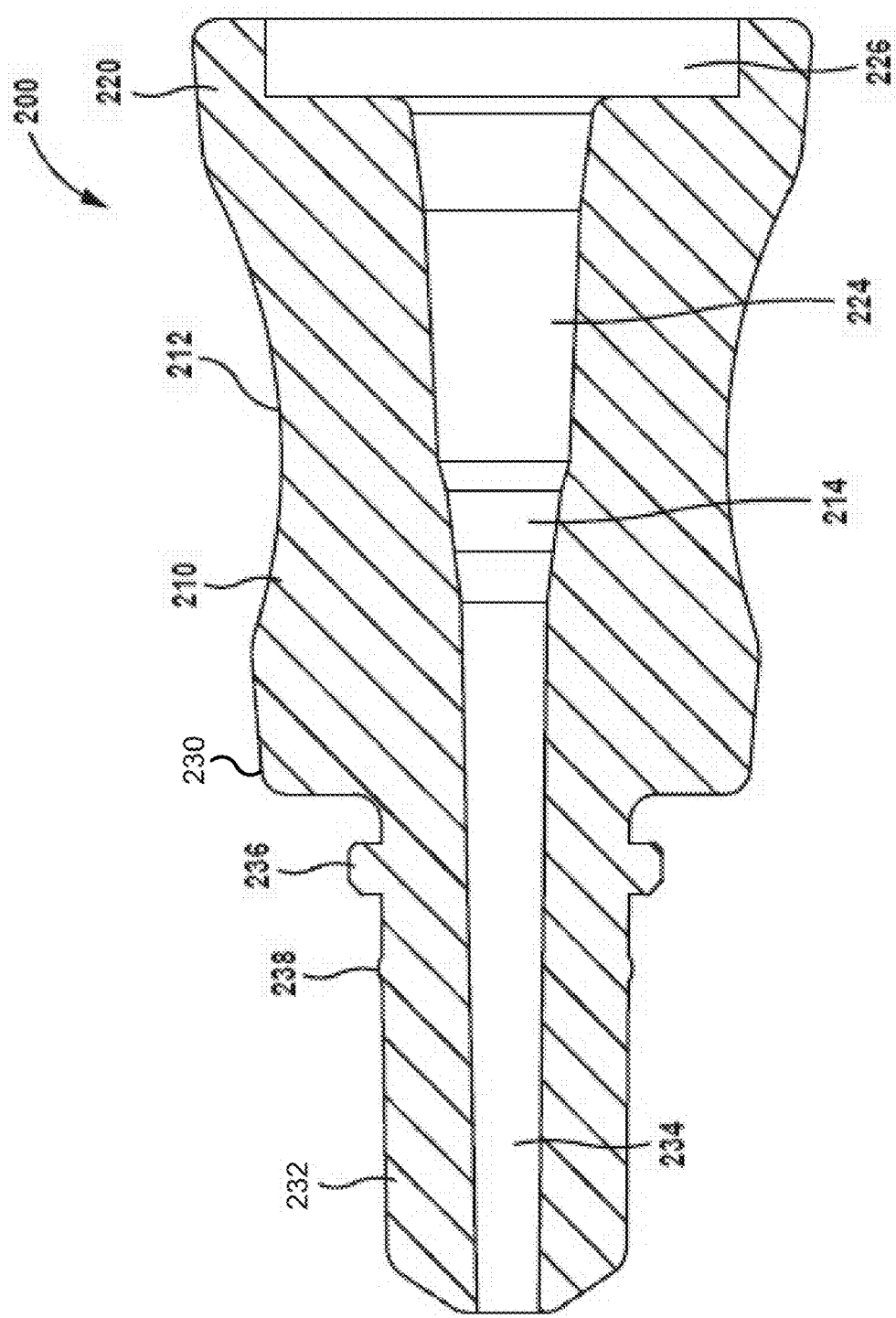
FIG. 4 is a side cross-section view of the coupler of FIG. 2 taken along the line A-A shown in FIG. 2.

In some embodiments, a coupler can include a male coupler configured to be coupled to a female coupling member or otherwise female coupling portion of a medical device, for example, an endoscope. Referring now to FIGS. 2-4, a coupler 200 includes a housing 210, a proximal portion 220 and a distal portion 230. A passageway 214 (FIG. 4) is defined between the proximal portion 220 and the distal portion 230. The proximal portion 220 is configured to be coupled to a fluid source (e.g., the fluid source 140) and the distal portion 230 is configured to be coupled to a medical device (e.g., the medical device 160) such that the medical device is in fluidic communication with the fluidic source via the passageway 214, as described herein.

The housing 210 or at least a portion of the housing 210 (e.g., the distal portion 230) can be formed from a deformable material such as, for example, an elastomer, polyurethane, silicone, rubber, urethane (e.g., QFLEX-ARP-90A-00-009 urethane) any other deformable material or combination thereof. In some embodiments, the hardness of the material used to form the housing 210 can be at least about 40 A, at least about 50 A, at least about 60 A, at least about 70 A, at least about 80 A, at least about 90 A, or at least about 100 A, inclusive of all ranges and values therebetween. In some embodiments, the hardness of the material used to form the housing 210 can be at least about 90 A. The housing 210 can be substantially cylindrical in shape, for example, resemble a frusto-conical cylinder. An outer surface of the housing 210 is tapered from the distal portion 230 to the proximal portion 220. Said another way, the proximal portion 220 can have an outer diameter, width or otherwise cross-section which is substantially larger than an outer diameter, width or otherwise cross-section of the distal portion 230 such that the housing 210 is tapered. A plurality of detents 212 are defined on an outer surface of the housing 210 (see e.g., FIGS. 2 and 3). The detents 212 can be configured to serve as grips to facilitate a user to easily grip the housing 210 for coupling the housing 210 to the medical device and/or the fluid source. Any number of detents 212 can be defined on the housing 210, for example, 2, 3, 4, 5, 6, or even more.

Figure 5:
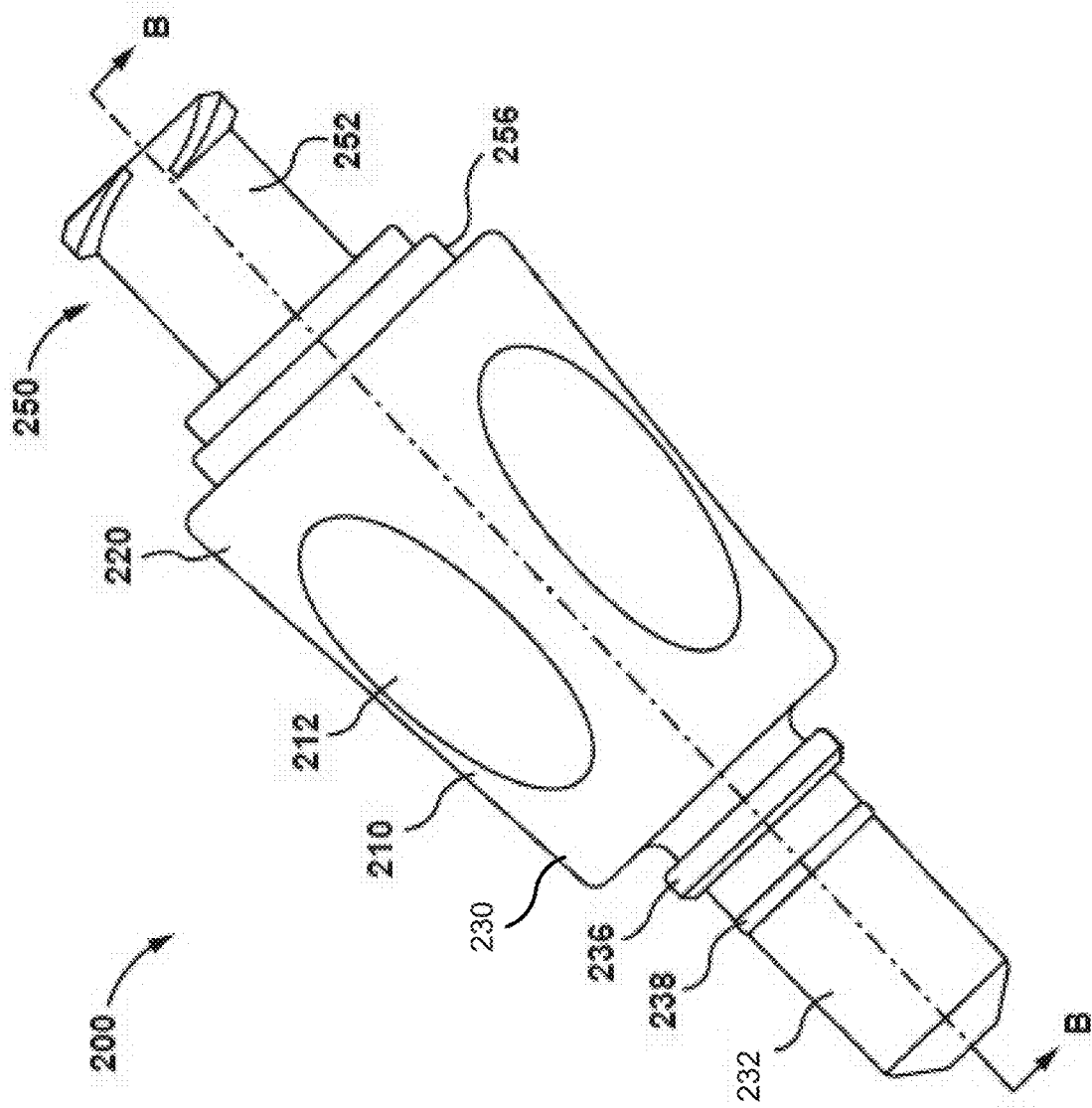
FIG. 5 is a perspective view of the coupler of FIG. 2 coupled with a fluidic connector.
Figure 6:
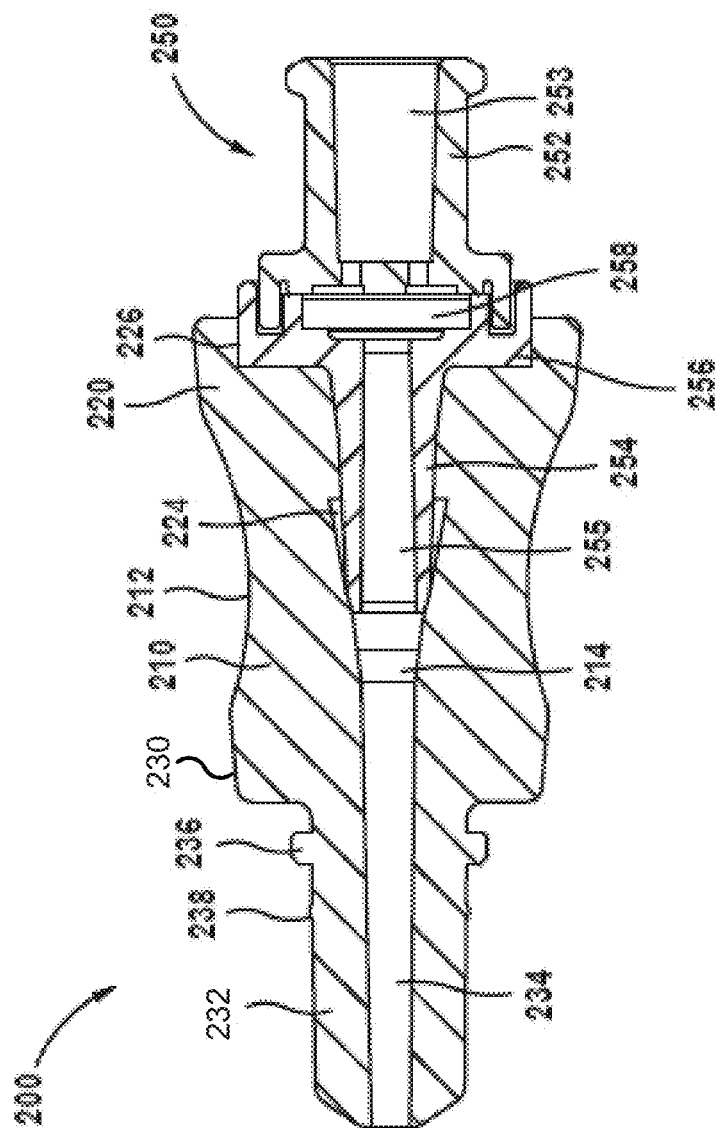
FIG. 6 is a side cross-section view of the coupler of FIG. 5 taken along the line B-B shown in FIG. 5.

The proximal portion 220 is configured to be coupled to the fluid source. Referring also now to FIGS. 5-6, a proximal end portion 224 of the passageway 214 can be configured to receive a distal end portion 254 of a fluidic connector 250. The fluidic connector 250 includes a proximal end portion 252 defining a first flow path 253 therethrough. The proximal end portion 252 can include Luer-lock connectors, threads, a snap-fit mechanism, a friction-fit mechanism, or any other suitable coupling mechanism configured to couple the fluidic connector 250 to the fluid source. The distal end portion 254 defines a second flow path 255, and is sized and shaped to be disposed within the proximal end portion 224 of the passageway 214. The proximal portion 220 defines a recess 226 configured to receive a shoulder 256 of the fluidic connector 250. In some embodiments, the recess 226 can be sized and shaped to be in close tolerance with an outer surface of the shoulder 256 of the fluidic connector 250, for example, to removably couple the fluidic connector 250 via a friction-fit mechanism. Furthermore, the shoulder 256 and the recess 226 can be collectively configured to allow the distal end portion 254 of the fluidic connector 250 to be inserted a known distance into the proximal end portion 224 of the passageway 214. A plurality of circumferential slots 228 (FIG. 3) can be defined in the proximal portion 220 radially about the proximal end portion 224 of the passageway 214. The circumferential slots 228 can be configured to increase the flexibility of a sidewall of the proximal end portion 224 of the passageway 214, for example, to facilitate insertion of the distal end portion 254 of the fluidic connector 250 into the proximal end portion 224 of the passageway 214. The fluidic connector 250 includes a valve 258 disposed between the proximal end portion 252 and the distal end portion 254 of the fluidic connector 250. The valve 258 (e.g., a check valve, a ball-check valve, a diaphragm, a butterfly valve, a septum valve, or any other suitable valve) can, for example, be a one way valve configured to allow fluid to flow in only direction, for example, from the first flow path 252 to the second flow path 254 of the fluidic connector 250 (i.e., only from the fluid source to the medical device). In some embodiments, the fluidic connector 250 can be removably coupled to the proximal portion 220. For example, the proximal portion 220 and/or the proximal end portion 224 of the passageway 214 can include a snap-fit mechanism, a friction-fit mechanism, threads, or a deformable portion, configured to removably couple the distal end portion 254 of the fluidic connector to the proximal portion 220. In some embodiments, the fluidic connector 250 can be fixedly coupled to the proximal portion 220. For example, the distal end portion 254 of the fluidic connector 250 can be fixedly coupled to the proximal end portion 224 of the passageway 214 using an adhesive, welding, heat sealing, solvent welding, fusion bonding, or the likes.

The distal portion 230 includes a protrusion 232 configured to be coupled to the medical device (e.g., the medical device 160 described herein). A distal end portion 234 of the passageway 214 is defined through the protrusion 234. The protrusion 232 extends distally from the distal portion 230 and is sized and shaped to be inserted into the medical device, for example, a lumen of a female coupling member (not shown) or otherwise coupling portion of the medical device. In this manner, the fluid source and the medical device can be brought into fluidic communication via the passageway 214 defined by the housing 210. A deformable member 236 is disposed on the protrusion 232 and configured to deform and removably couple the housing 210 to the medical device. As shown in FIG. 2, the deformable member 236, includes a ridge disposed circumferentially on an outer surface of the protrusion 232 and configured to deform when the protrusion 232 is inserted (e.g., press fitted) into the lumen of the female coupling member. The deformable member 236 can be formed from a substantially deformable material such as, for example, an elastomer, polyurethane, silicone, rubber, urethane (e.g., QFLEX-ARP-90A-00-009 urethane) any other deformable material or combination thereof. In some embodiments, the deformable member 236 can be monolithically formed with the protrusion 232. In some embodiments, the deformable member 236 can be manufactured separately and coupled to the protrusion 232 using any suitable means, for example, an adhesive, hot welding, fusion bonding, etc. In such embodiments, the housing 210 and the deformable member 236 can be formed from separate materials. For example, the housing 210 can be formed from a first material, for example, a substantially rigid material (e.g., having a Shore D hardness of at least about 100 D), and the deformable member 236 can be formed from a second material, for example, a substantially deformable material (e.g. having a Shore A hardness of less than about 90 A), as described herein. Thus, the deformable member 236 can deform when the protrusion 232 is inserted into the lumen defined by the female coupling member and conform to an inner surface of the lumen. The deformation can, for example, create a high friction interface with the inner surface of the lumen which removably couples the housing 210 to the medical device, for example, a female coupling member or otherwise portion of the medical device. In some embodiments, the protrusion 232 can be tapered distally relative to the distal portion 230, for example, define a taper angle of about 1 degrees, 2 degrees, 3 degrees, 4 degrees, 5 degrees, or any other suitable taper angle. In this manner, when the protrusion 232 is inserted or pressed into the lumen of the female coupling member, the deformation of the deformable member 236 and/or an elastic force exerted by the deformable member 236 against the lumen or an inlet of the lumen of the female coupling member can increase. In some embodiments, the female coupling member of the medical device can have a plurality of female threads. In such embodiments, the deformable member 236 can be configured to deform and mate with at least a portion of the plurality of female threads to removably couple the housing 210 to the medical device. In some embodiments, the deformable member 236 can also form a substantially fluid-tight seal with the female coupling member of the medical device. For example, the protrusion 232 can be inserted into the lumen of the female coupling member with a suitable insertion force, for example, an insertion force of about 5 lbs., 6 lbs., 7 lbs., 8 lbs., 9 lbs., 10 lbs., or any other suitable force such that the deformable member 236 can form a substantially fluid-tight seal against at least a portion of the plurality of threads (or otherwise lumen) of the female coupling member. In some embodiments, the housing 210 can be coupled to the medical device using manual force without using tools, such that the manual force is sufficient to urge the deformable member 236 to form a fluid tight seal with the lumen of the female coupling member. In some embodiments, the housing 210 does not have to be rotated, twisted, or otherwise turned to insert the protrusion 232 into the lumen of the female coupling member (e.g., a lumen having a plurality of threads disposed on an inner surface of the lumen). In such embodiments, the protrusion 232 can be press-fitted into the lumen defined by the female coupling member to urge the deformable member to deform and removably couple the housing 210 to the medical device via the female coupling member. The coupling of the housing 210 to the female coupling member can be sufficiently strong to prevent uncoupling of the female coupling member from the housing 210 accidentally or because of a fluidic backpressure on the housing 210 or the female coupling member. Furthermore, the strength of the coupling can be configured such that a manual force above a predetermined threshold can be sufficient to uncouple the housing 210 from the female coupling member.

In some embodiments, a sealing member 238 can also be disposed on the protrusion 232. As shown in FIG. 2 the sealing member 238 is disposed distally relative to the deformable member 236. The sealing member 238 includes a circular rib resembling an O-ring. In some embodiments, the sealing member 238 can be monolithically formed with the protrusion 232. In some embodiments, the sealing member 238 can be formed separately and thereafter, disposed on the protrusion 232. For example, the sealing member 238 can include an O-ring which is disposed in a circumferential groove defined on the protrusion 232. The sealing member 238 can be configured to form a substantially fluid-tight seal with the medical device, for example, the lumen of the female coupling member of the medical device. For example, the sealing member 238 can be disposed distally relative to a plurality of threads defined by the lumen of the female coupling member when the protrusion 232 is inserted into the lumen. The sealing member 238 can be configured to form a substantially fluid-tight seal with the lumen of the female coupling member, thus ensuring that the coupling of the housing 210 to the medical device creates a substantially fluid-tight seal even if the deformable member 236 is not configured or able to form a substantially fluid-tight seal, or suffer from leakage, for example, due to high fluid pressure. Said another way, the sealing member 238 and the deformable member 236 can collectively form a double seal. In some embodiments, the sealing member 238 can be substantially rigid such that the sealing member 238 does not deform when the protrusion 232 is inserted into the lumen of the female coupling member or otherwise female coupling portion of the medical device. In some embodiments, the sealing member 238 can be formed from a substantially deformable material, for example, formed from the same material as the deformable member 236.

Figure 7:
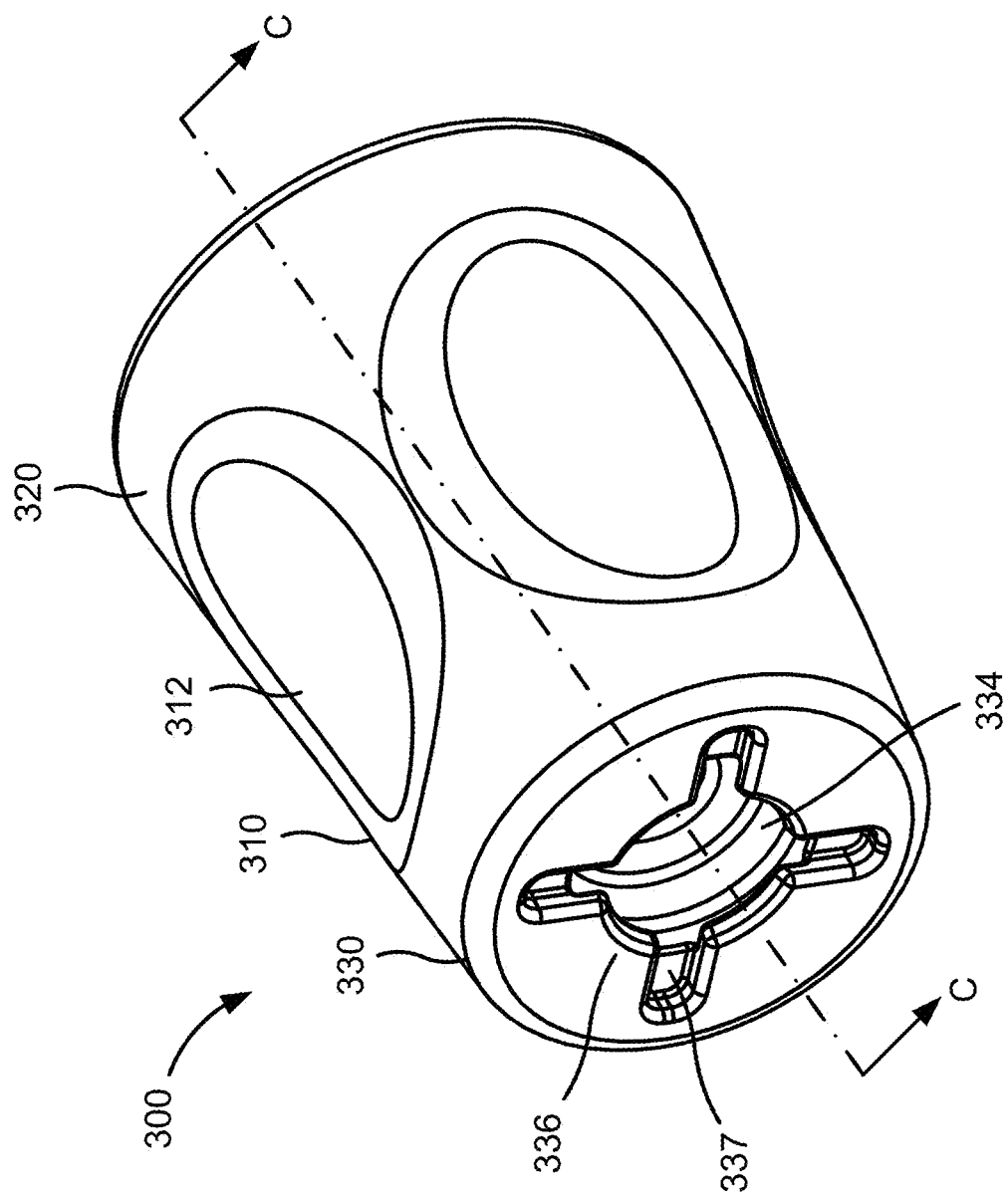
FIG. 7 is a front perspective view of a coupler, according to an embodiment.
Figure 8:
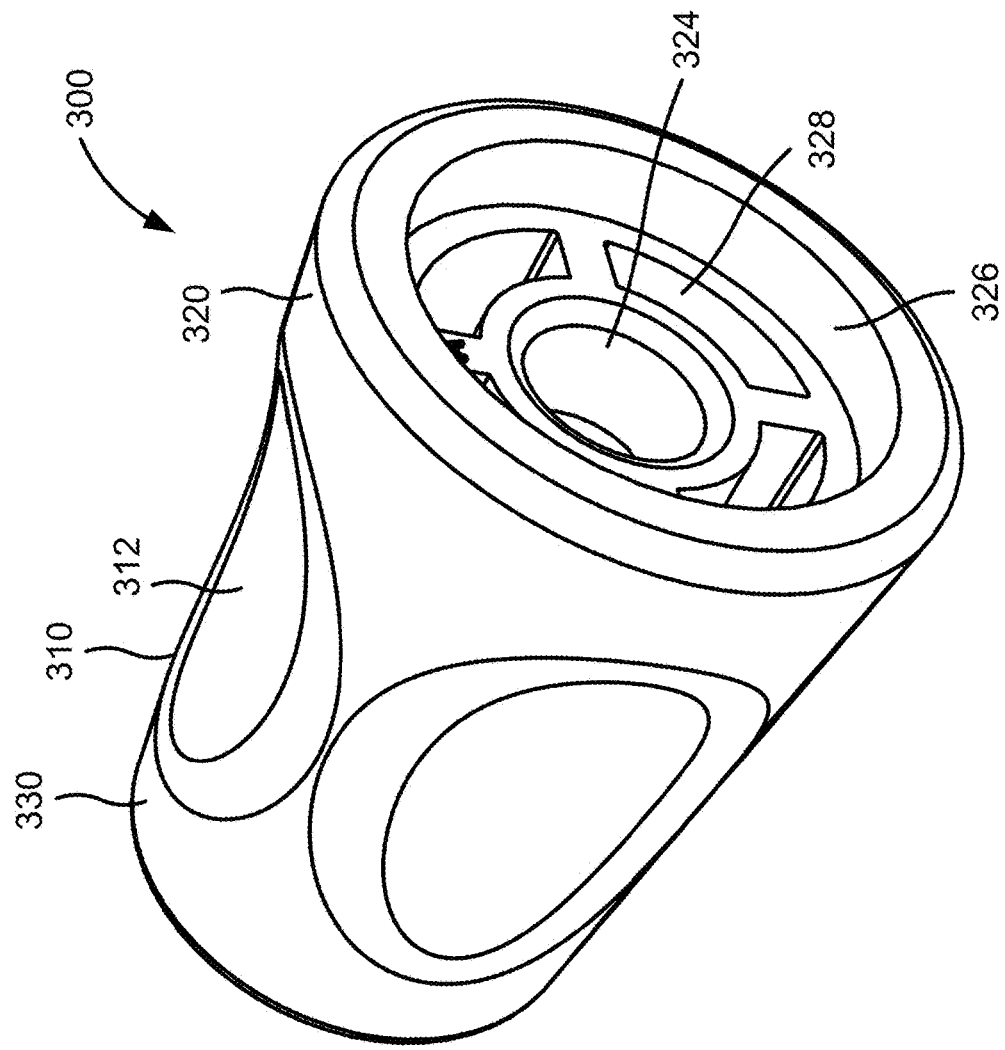
FIG. 8 is a back perspective view of the coupler of FIG. 7.
Figure 9:
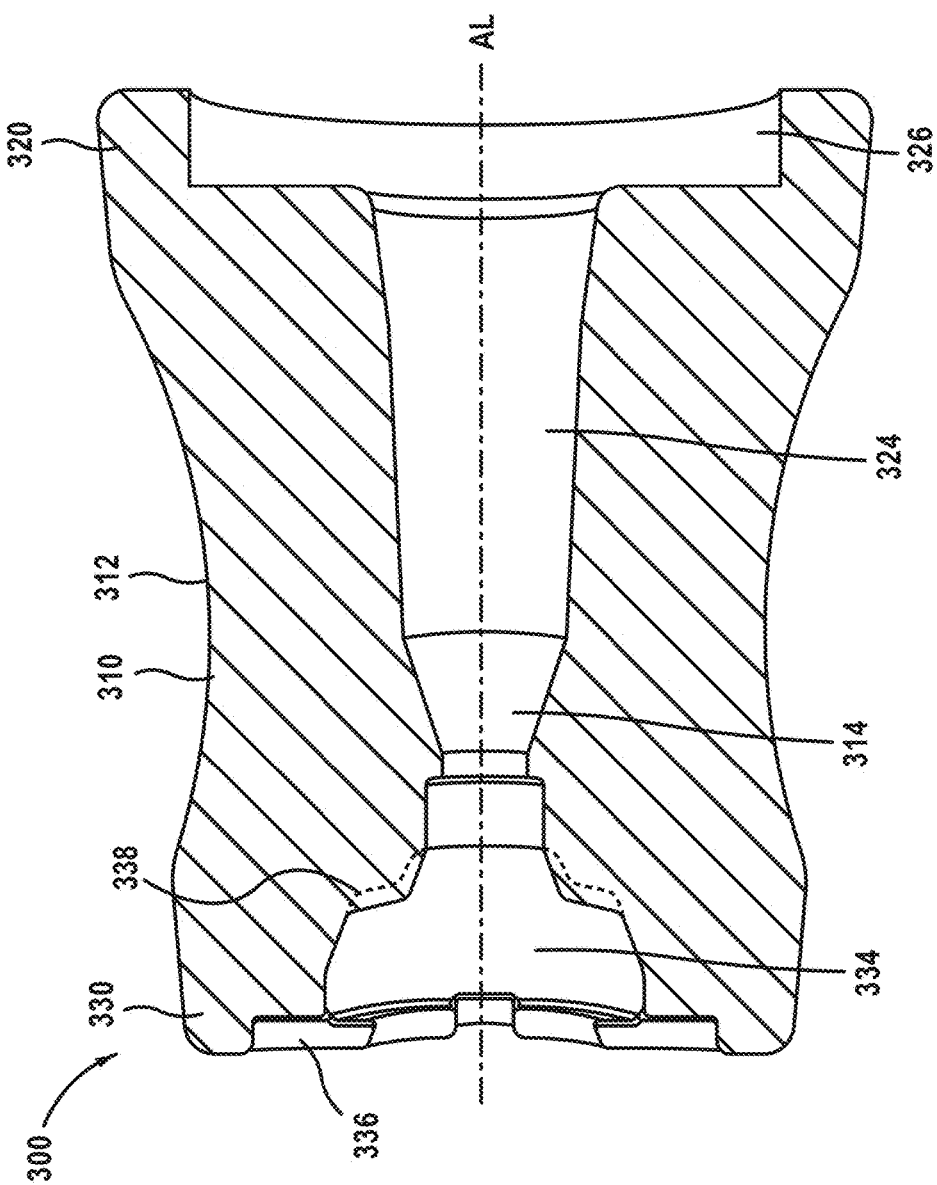
FIG. 9 is a side cross-section view of the coupler of FIG. 7 taken along the line C-C shown in FIG. 7.
Figure 10:
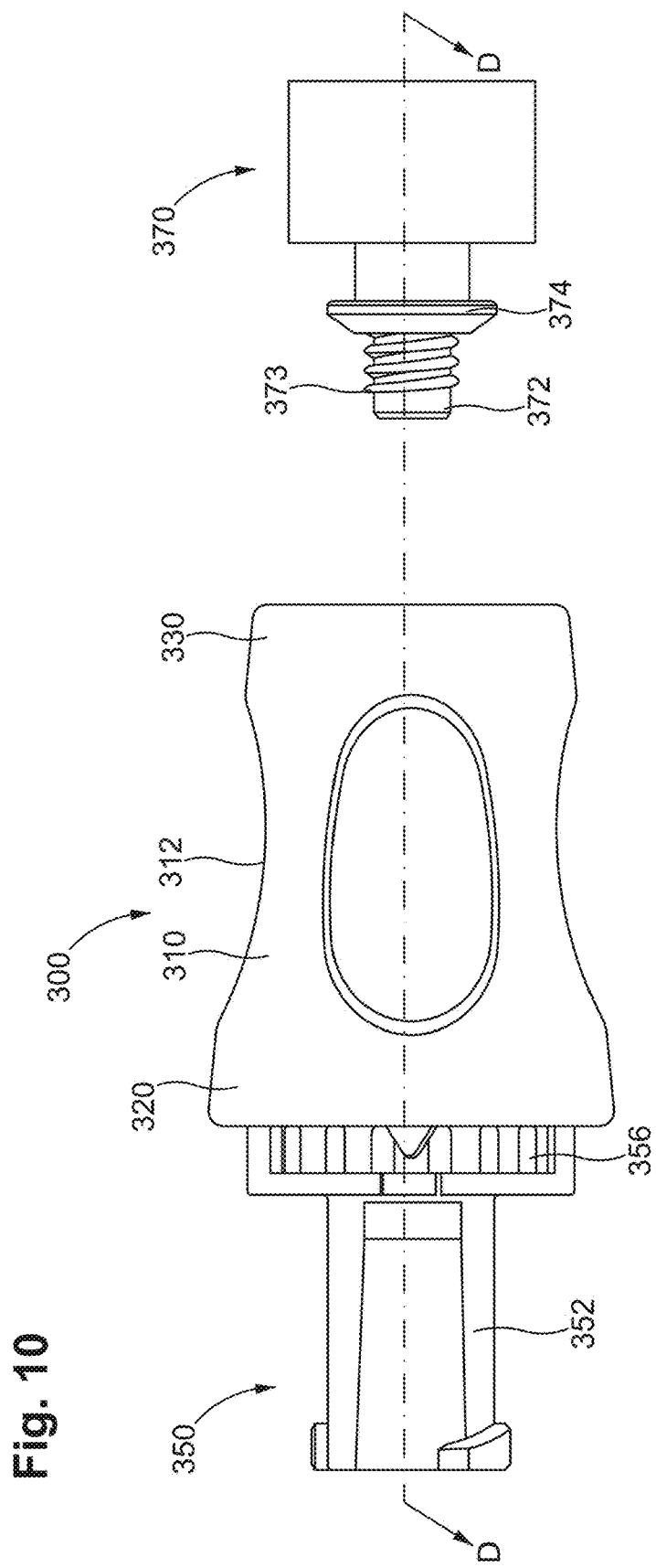
FIG. 10 is a side view of the coupler of FIG. 7 in a first configuration with a fluidic connector coupled thereto and male coupling member of a medical device configured to be coupled with the coupler.

In some embodiments, a coupler can include a female coupler configured to be coupled to a male coupling member or otherwise male coupling portion of a medical device, for example, an endoscope. Referring now to FIGS. 7-9, a coupler 300 includes a housing 310, a proximal portion 320 and a distal portion 330. A passageway 314 (FIG. 9) is defined between the proximal portion 320 and the distal portion 330. The proximal portion 320 is configured to be coupled to a fluid source (e.g., the fluid source 140) and the distal portion 330 is configured to be coupled to a medical device (e.g., the medical device 160) such that the medical device is in fluidic communication with the fluidic source via the passageway 314, as described herein.

The housing 310 or at least a portion of the housing 310 (e.g., the distal portion 330) can be formed from a deformable material such as, for example, an elastomer, polyurethane, silicone, rubber, urethane (e.g., QFLEX-ARP-90A-00-009 urethane) any other deformable material or combination thereof. In some embodiments, the hardness of the material used to form the housing 210 can be at least about 40, at least about 50 A, at least about 60 A, at least about 70 A, at least about 80 A, at least about 90 A, or at least about 100 A, inclusive of all ranges and values therebetween. In some embodiments, the hardness of the material used to form the housing 210 can be at least about 90 A. The housing 310 can be substantially cylindrical in shape, for example, resemble a frusto-conical cylinder. An outer surface of the housing 310 is tapered from the distal portion 330 to the proximal portion 320. Said another way, the proximal portion 320 can have an outer diameter, width or otherwise cross-section which is substantially larger than an outer diameter, width or otherwise cross-section of the distal portion 330 such that the outer surface of the housing 310 is tapered. A plurality of detents 312 are defined on an outer surface of the housing 310. The detents 312 can be configured to serve as grips to facilitate a user to easily grip the housing 310 for coupling the housing 310 to the medical device and/or the fluid connector. Any number of detents can be defined on the housing 310, for example, 2, 3, 4, 5, 6, or even more.

Figure 11:
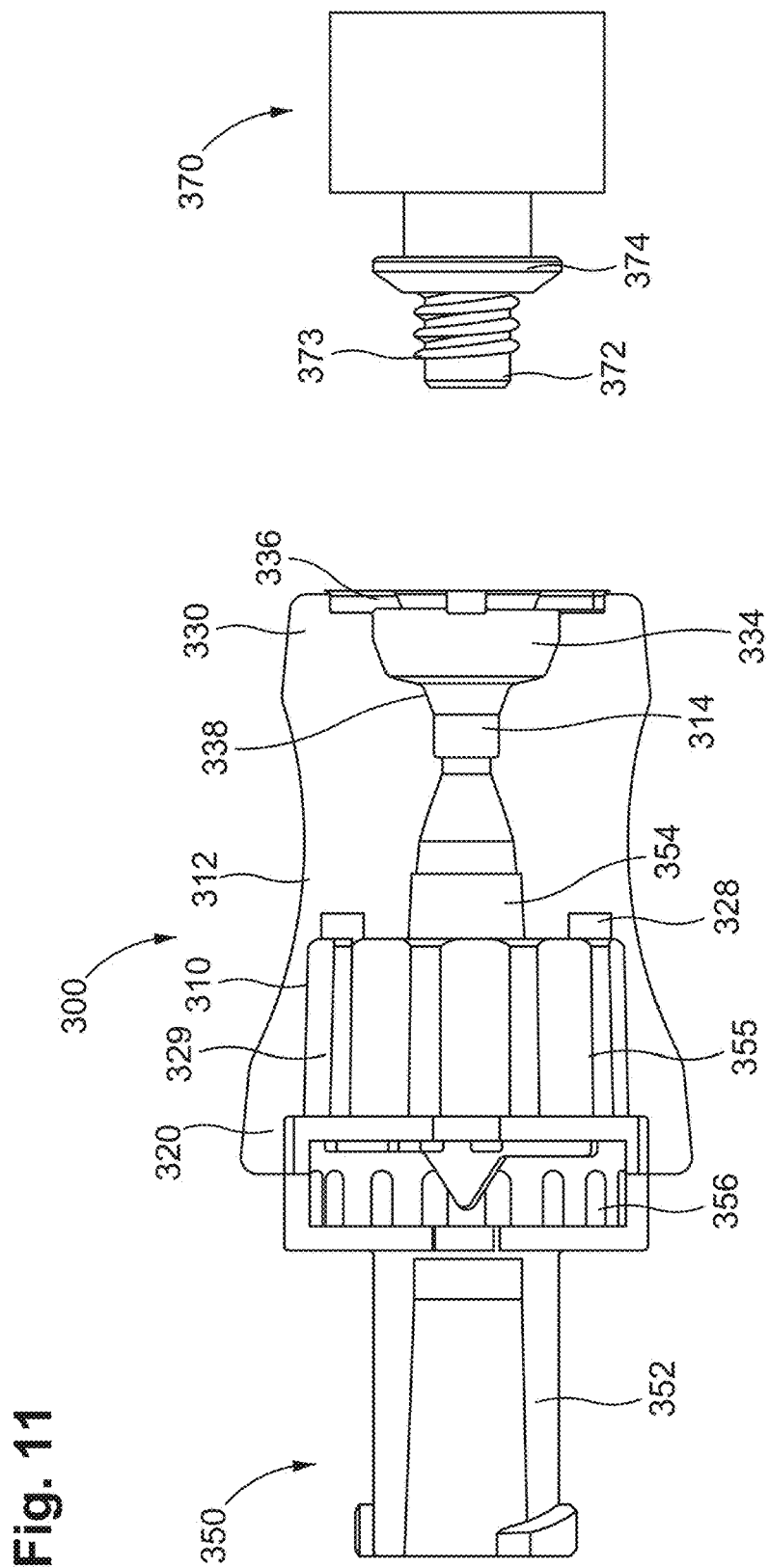
FIG. 11 is a side cross-section view of the coupler of FIG. 10 taken along the line D-D shown in FIG. 10.
Figure 12:
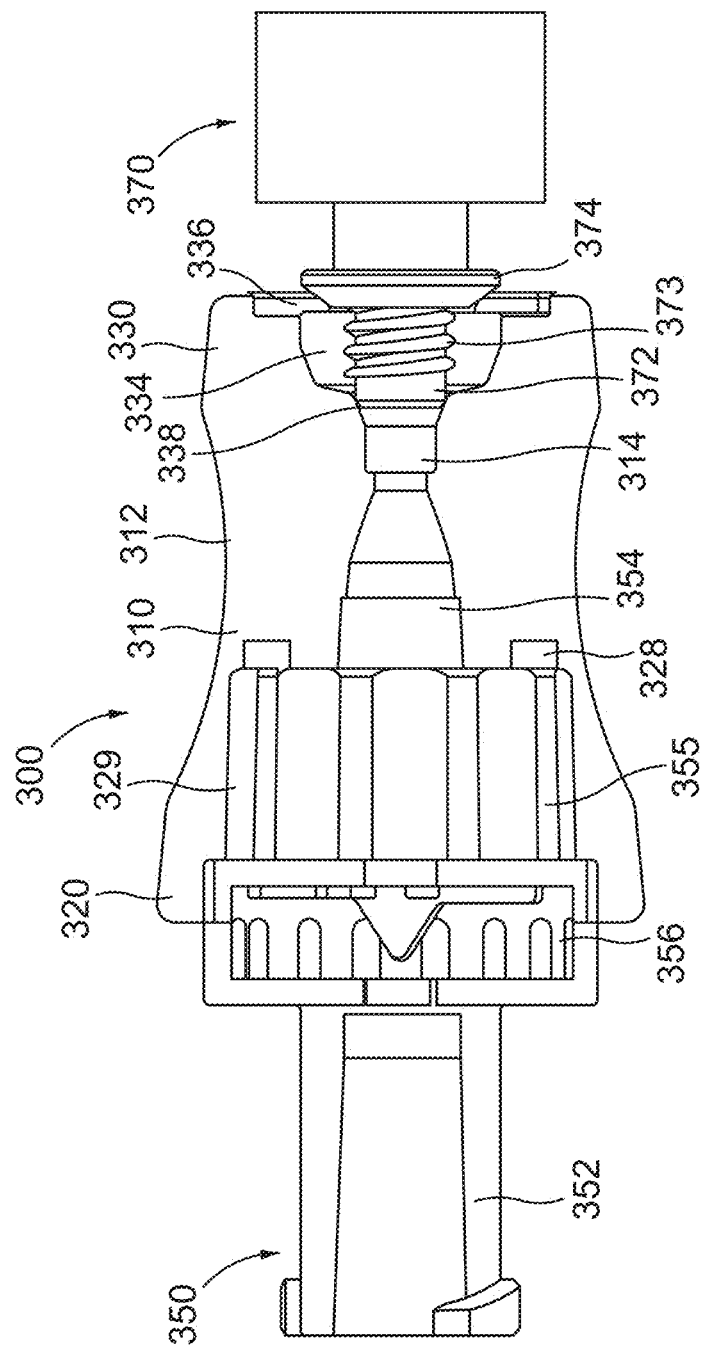
FIG. 12 is a side cross-section view of the coupler of the FIG. 10 in a second configuration showing an engagement member of the male coupling member engaging a deformable member included in the coupler 300.
Figure 13:
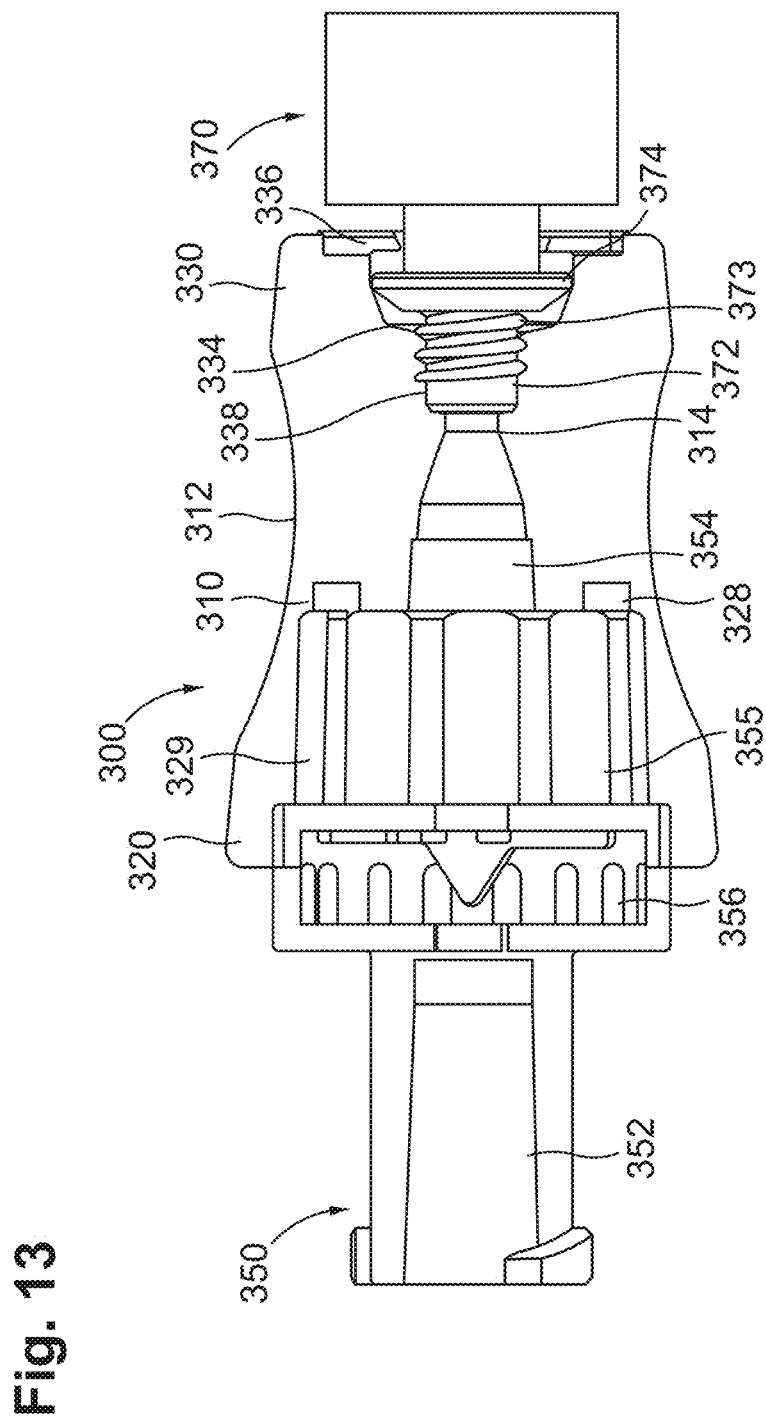
FIG. 13 is a side cross-section view of the coupler of FIG. 10 in a third configuration showing a protrusion included in the male coupling member engaging a sealing portion define by the coupler.

The proximal portion 320 is configured to be coupled to the fluid source. Referring also now to FIGS. 10-13, a proximal end portion 324 of the passageway 314 (FIG. 9) can be configured to receive at least a portion of a fluid connecter 350, or any other fluid connector described herein (e.g., the fluidic connector 250). The fluidic connector 350 can define a second flow path therethrough configured to communicate fluid from an external fluid reservoir to the medical device via the coupler 300, as described herein. FIG. 11 shows a side cross-section of the coupler 300 in a first configuration in which the fluidic connector 350 is coupled to the proximal portion 320 of the coupler 300 and a male coupling member 370 is uncoupled with the coupler 300. The proximal portion 320 defines a recess 326 configured to receive a shoulder 356 defined by the fluidic connector 350. As shown in FIGS. 11-13, the recess 326 can be sized and shaped to be in close tolerance with an outer surface of the shoulder 356 of the fluidic connector 350, for example, to removably couple the fluidic connector 350 via a friction-fit mechanism. Furthermore, the shoulder 356 and the recess 326 can be collectively configured to allow the distal end portion 354 of the fluidic connector 350 to be inserted a known distance into the proximal end portion 324 of the passageway 314. A plurality of circumferential slots 328 (FIGS. 8 and 10) can be defined in the proximal portion 320 radially about the proximal end portion 324 of the passageway 314. The circumferential slots 328 can be configured to increase the flexibility of a sidewall of the proximal end portion 324 of the passageway 314, for example, to facilitate insertion of the distal end portion 354 of the fluidic connector 350 into the proximal end portion 324 of the passageway 314 and form a press-fit coupling with at least a portion of the fluidic connector 350. For example, as shown in FIG. 11, the sidewall of the proximal portion end portion 324 of the passageway 314 can define a coupling portion 329 which deforms to receive a medial portion 355 of the fluidic connector 350. Furthermore, a distal end portion 354 of the fluidic connector 350, which can, for example, a nozzle or a fluidic outlet, can be disposed inside the passageway 314. At least a portion of the sidewall of the passageway 314 can also deform to receive the distal end portion 354 of the fluidic connector, thereby allowing a substantially fluid tight seal to be formed between the distal end portion 354 of the fluidic connector 350 and the passageway 314. In this manner, the fluidic connector 350 can be removably coupled to the proximal portion 320. In some embodiments, the fluidic connector 350 can be fixedly coupled to the proximal portion 320. For example, the distal end portion 354 of the fluidic connector 350 can be fixedly coupled to the proximal end portion 324 of the passageway 314 using an adhesive, welding, heat sealing, solvent welding, laser welding, fusion bonding, or the likes.

The distal portion 330 is configured to be coupled to a male coupling member or otherwise male coupling portion of the medical device. As shown in FIGS. 10-13, the distal portion 330 can be configured to be coupled to a male coupling member 370, which can be included in the medical device. The male coupling member 370 includes a protrusion 372 disposed on a proximal end of the male coupling member 370. A plurality of threads 373 are defined on the protrusion 372. An engagement member 374 is disposed on the protrusion 372. In some embodiments, the engagement member 374 can be a circumferential ridge. In some embodiments, the engagement member 373 can also include threads. The male coupling member 370 defines a flow path therethrough configured to communicate fluid received from the fluid source to the medical device received via the passageway 314.

The distal portion 330 defines a recess 334 (shown in FIGS. 9 and 11-13) configured to receive the protrusion 372 of the male coupling member 370 and thereby, couple the housing 310 to the male coupling member 370 (thus coupling the medical device to the housing 310). In some embodiments, at least a portion of the male coupling member 370, for example, the engagement member 373 can have a plurality of threads and the inner surface of the recess 334 can be configured to deform to mate with the threads and removably couple the housing 310 to the male coupling member 370 and thereby, the medical device.

A deformable member 336 is disposed in the recess 334 (FIGS. 7, 9 and 11-13) and configured to deform to couple the housing 310 to the male coupling member 370, thereby coupling the housing 310 to the medical device. The deformable member 336 includes a substantially planar member which can resemble a flap. The deformable member 336 is disposed orthogonal to a longitudinal axis $A_L$ of the housing 310 at an entrance of the recess 334 (FIG. 9). The deformable member 336 can be configured to deform, for example, bend or flex, when the protrusion 372 of the male coupling member 370 is inserted (e.g., press fitted) into the recess 334. A plurality of slots 337 (FIG. 7) are defined in the deformable member 336 which are configured to allow deformation (e.g., increase or otherwise enhance the deformation) of the deformable member 336, for example, when the protrusion 372 of the male coupling member 370 is inserted into the recess 334. The deformable member 336 defines a central pathway through which the protrusion 372 of the male coupling member 370 can be inserted into the recess 334. The protrusion 372 and/or the engagement member 374 disposed on the protrusion 372 can have a size or otherwise cross-section configured to interfere with the deformable member 336 during the insertion. This can urge the deformable member 336 to deform (e.g., bend) substantially and allow the protrusion 372 and the engagement member 374 disposed thereon to be inserted into the recess 334 to couple the housing 310 to the male coupling member 370 and thereby, the medical device. For example, FIG. 12 shows a side cross-section of the coupler 300 in a second configuration in which the male coupling member 370 is partially coupled with the distal end portion 330 of the coupler 300. In the second configuration, at least a portion of the protrusion 372 is disposed in the recess 334 and the engagement member 374 is in contact with the deformable members 336 urging the deformable member 336 into a deformed configuration. The male coupling member 370 can then be moved proximally relative to the coupler 300, i.e., further into the recess 334 (e.g., rotated into the recess 334 or pushed into the recess 334 without any rotation) to urge the coupler 300 into a third configuration shown in FIG. 13. In the third configuration, the engagement member 374 continues engaging the deformable member 336 to further deform the deformable members 374 until the engagement member 374 is also disposed in the recess 334. The deformable member 336 can return to its undeformed configuration in third configuration and can, for example, contact a portion of the protrusion 372 distal relative to the engagement member 374. In some embodiments the deformable member 336 can form a substantially fluid-tight seal with the portion of the protrusion 372 of the male coupling member 370. In such embodiments, the slots 337 can be excluded from the deformable member 336. In some embodiments, the deformable member 336 can be configured to exert a force on a portion of the male coupling member 370, for example, the engagement member 374, for example, a force of about 3 lbs., 4 lbs., 5 lbs., 6 lbs., 7 lbs., 8 lbs., 9 lbs., or 10 lbs., inclusive of all ranges therebetween. The force can, for example, prevent the male coupling member 370 (and thereby the medical device) from uncoupling from the housing 110. For example, the deformable member 336 can return to its undeformed position once the protrusion 372 and the engagement member 374 disposed thereon (FIG. 13) are disposed in the recess 334. The deformable member 334 can then apply a force on the engagement member 374 of the male coupling member 370 preventing uncoupling, for example, inadvertent or accidental uncoupling of the male coupling member 370 from the housing 310, or uncoupling due to a fluidic backpressure experienced by the housing 310 and/or the male coupling member 370. Moreover, the deformable member 336 can be configured such that the when a force above a predetermined threshold is applied on the male coupling member 370, or otherwise the medical device, the male coupling member 370 is uncoupled from the housing 310. In this manner, the deformable member 336 can enable removable coupling of the male coupling member 370 to the housing 310. In some embodiments, the force can be low enough to allow manual coupling and/or uncoupling of the male coupling member 370 to the housing 310 without using tools.

In some embodiments, a sealing portion 338 can be disposed in the recess 334 (shown by dotted line in FIG. 9) and configured to substantially deform to form a substantially fluid-tight seal with the male coupling member 370. The sealing portion 338 includes at least portion of an inner surface of the recess 334 proximate to the passageway 314 which is substantially deformable, for example, formed from a substantially deformable material. The sealing portion 338 can be configured to deform and thereby, conform to an outer surface of a proximal end of the protrusion 372 of the male coupling member 370. For example, as shown in FIG. 12, in the second configuration the protrusion 372 can be inserted (e.g., press-fit) into the recess, until an outer surface of the proximal end of the protrusion 372 contacts the sealing portion 338 and deforms the sealing portion 338. The protrusion 372 can be inserted further into the recess 334, for example, press fitted or otherwise rotated into the recess such that the threads 373 disposed on the proximal end of the protrusion 372 deform the sealing portion 338. This can urge the sealing portion 338 to deform to the threads 373 disposed on the proximal end of the protrusion 372. In this manner, the sealing portion 338 can form a substantially fluid-tight seal between the housing 310 and the male coupling member 370, as well as removably couple the coupler 300 to the male coupling member 370 of the medical device.

While various embodiments of the system, methods and devices have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. For example, while the coupler 300 is shown coupled to the male coupling member 370, the coupler 300 can be coupled to any male coupling member, for example, a male coupling that does not include the engagement member 374 or threads 373 defined on the protrusion 372.

In addition, the specific configurations of the various components can also be varied. For example, the size and specific shape of the various components can be different than the embodiments shown, while still providing the functions as described herein.

The invention claimed is:

1. A device for fluidically coupling a fluid source to a medical device, the device comprising:
   a housing including a proximal portion and a distal portion and defining a passageway therebetween, the proximal portion configured to be coupled to the fluid source and the distal portion configured to be coupled to the medical device such that the medical device is in fluidic communication with the fluid source via the passageway; and
   a threadless deformable member disposed on the distal portion and configured to deform and removably couple the housing to form a substantially fluid tight seal with the medical device, wherein the medical device includes a coupling portion having a plurality of male threads, the threadless deformable member configured to deform and engage with at least a portion of the plurality of male threads to couple the housing to the medical device.

2. The device of claim 1, further comprising;
a sealing member disposed on the distal portion of the housing and configured to form a substantially fluid tight seal with the medical device.

3. The device of claim 1, further comprising:
a valve disposed in the passageway, the valve configured to prevent any back flow of fluid from the medical device to the fluid source.

4. The device of claim 1, wherein the housing includes a plurality of detents defined on an outer surface of the housing.

5. The device of claim 1, wherein the threadless deformable member includes a flexible elastomeric material having a 90 Shore A hardness.

6. The device of claim 5, wherein the threadless deformable member is formed from urethane.

7. The device of claim 1, wherein the threadless deformable member is configured to non-permanently change shape when coupling, with at least a portion of the plurality of male threads to couple the housing to the medical device.

8. The device of claim 1, wherein the threadless deformable member is configured to press-fit with at least a portion of the plurality of male threads to couple the housing to the medical device.

9. The device of claim 8, wherein the threadless deformable member configured to press-fit with at least a portion of the plurality of male threads to couple the housing to the medical device is configured to couple to the medical device without having to rotate the housing and/or the medical device.

10. A device for fluidically coupling a fluid source to a medical device, the device comprising:
a housing including a proximal portion and a distal portion and defining a passageway therebetween, the proximal portion configured to be coupled to the fluid source and the distal portion configured to be coupled to the medical device such that the medical device is in fluidic communication with the fluid source via the passageway; and
a threadless deformable member disposed on the distal portion and configured to deform and removably couple the housing to form a substantially fluid tight seal with the medical device, wherein the medical device includes a coupling portion having a plurality of female threads, the threadless deformable member configured to deform and engage with at least a portion of the plurality of female threads to couple the housing to the medical device.

11. The device of claim 10, further comprising;
a sealing member disposed on the distal portion of the housing and configured to form a substantially fluid tight seal with the medical device.

12. The device of claim 10, further comprising:
a valve disposed in the passageway, the valve configured to prevent any back flow of fluid from the medical device to the fluid source.

13. The device of claim 10, wherein the housing includes a plurality of detents defined on an outer surface of the housing.

14. The device of claim 10, wherein the threadless deformable member includes a flexible elastomeric material having a 90 Shore A hardness.

15. The device of claim 14, wherein the threadless deformable member is formed from urethane.

16. The device of claim 10, wherein the threadless deformable member is configured to non-permanently change shape when coupling with at least a portion of the plurality of female threads to couple the housing to the medical device.

17. The device of claim 10, wherein the threadless deformable member is configured to press-fit with at least a portion of the plurality of female threads to couple the housing to the medical device.

18. The device of claim 17, wherein the threadless deformable member configured to press-fit with at least a portion of the plurality of female threads to couple the housing to the medical device is configured to couple to the medical device without having to rotate the housing and/or the medical device.

* * * * *

UNITED STATES PATENT AND TRADEMARK OFFICE
CERTIFICATE OF CORRECTION

| | |
|---|---|
| PATENT NO. | : 10,052,472 B2 |
| APPLICATION NO. | : 14/529967 |
| DATED | : August 21, 2018 |
| INVENTOR(S) | : Daniel G. Maurice |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 711 days.

Signed and Sealed this
Twenty-third Day of April, 2019

Andrei Iancu
*Director of the United States Patent and Trademark Office*